United States Patent [19]

Wolman

[11] Patent Number: 5,549,567
[45] Date of Patent: Aug. 27, 1996

[54] INFUSION ADMINSTERING CATHETER HOLDER

[76] Inventor: Michael Wolman, 5, Haim VeElisha Street, Tel-Aviv, Israel

[21] Appl. No.: 325,779

[22] Filed: Oct. 19, 1994

[30] Foreign Application Priority Data

Oct. 27, 1993 [IL] Israel .......................... 107411

[51] Int. Cl.⁶ .................................................. A61M 25/02
[52] U.S. Cl. ...................... 604/179; 138/DIG. 26
[58] Field of Search .................... 128/DIG. 26; 604/174, 604/179, 190

[56] References Cited

U.S. PATENT DOCUMENTS

| | | | |
|---|---|---|---|
| 3,046,984 | 7/1962 | Eby | 128/DIG. 26 |
| 3,059,645 | 10/1962 | Hasbrouck et al. | 604/179 |
| 3,160,158 | 12/1964 | Rayhart | 604/179 |
| 3,765,421 | 10/1973 | Poprik | 604/179 |
| 4,059,105 | 11/1977 | Cutruzzula et al. | 128/DIG. 26 |
| 4,088,136 | 5/1978 | Hasslinger et al. | 128/DIG. 26 |
| 4,096,863 | 6/1978 | Kaplan et al. | 604/179 |
| 4,445,894 | 5/1984 | Rovaks | 604/179 |
| 4,470,410 | 9/1984 | Elliott | 128/DIG. 26 |
| 4,571,245 | 2/1986 | Hubbard et al. | 604/179 |
| 4,591,356 | 5/1986 | Christie | 604/179 |
| 4,671,787 | 6/1987 | Widman . | |
| 4,726,716 | 2/1987 | McGuire | 604/186 |
| 4,799,923 | 1/1989 | Campbell | 128/DIG. 26 |
| 5,037,397 | 8/1991 | Kalt et al. | 604/174 |
| 5,076,289 | 12/1991 | Darling | 128/DIG. 6 |
| 5,188,608 | 2/1993 | Frihs | 604/179 |
| 5,342,317 | 8/1994 | Claywell | 604/177 |
| 5,413,562 | 5/1995 | Swauger | 128/DIG. 26 |

FOREIGN PATENT DOCUMENTS 1405075  12/1965  France .
3237176  4/1984  Germany .

OTHER PUBLICATIONS

European Search Report listing the above cited references.

Primary Examiner—Paul J. Hirsch
Attorney, Agent, or Firm—Kane, Dalsimer, Sullivan, Kuruz, Levy, Eisele and Richard, LLP

[57] ABSTRACT

A holder for infusion administering catheter devices which comprise a head portion and a catheter portion, is formed as deformable band, having a first portion configured to overlie the device in its administered position onto a patient's arm without obstructing access to its functional parts, and a second portion adapted to surround the arm portion of the patient and become tightened over the said first portion by releasable attaching means. In an embodiment the holder is made of an elastic material, such as silicone rubber or a BVS K-Resin. The releasable attaching means may be VELCRO or core fasteners, such as mushrooms fasteners.

16 Claims, 4 Drawing Sheets

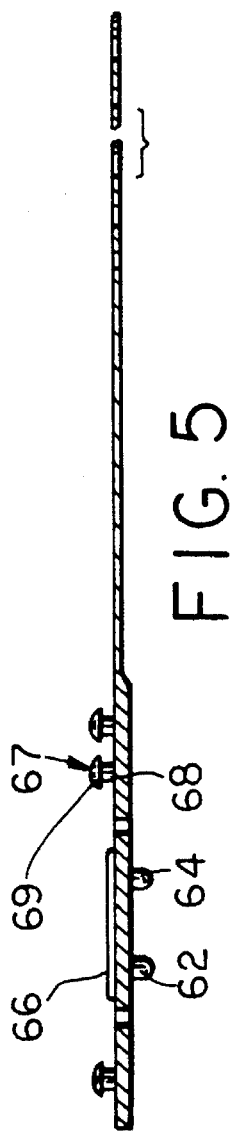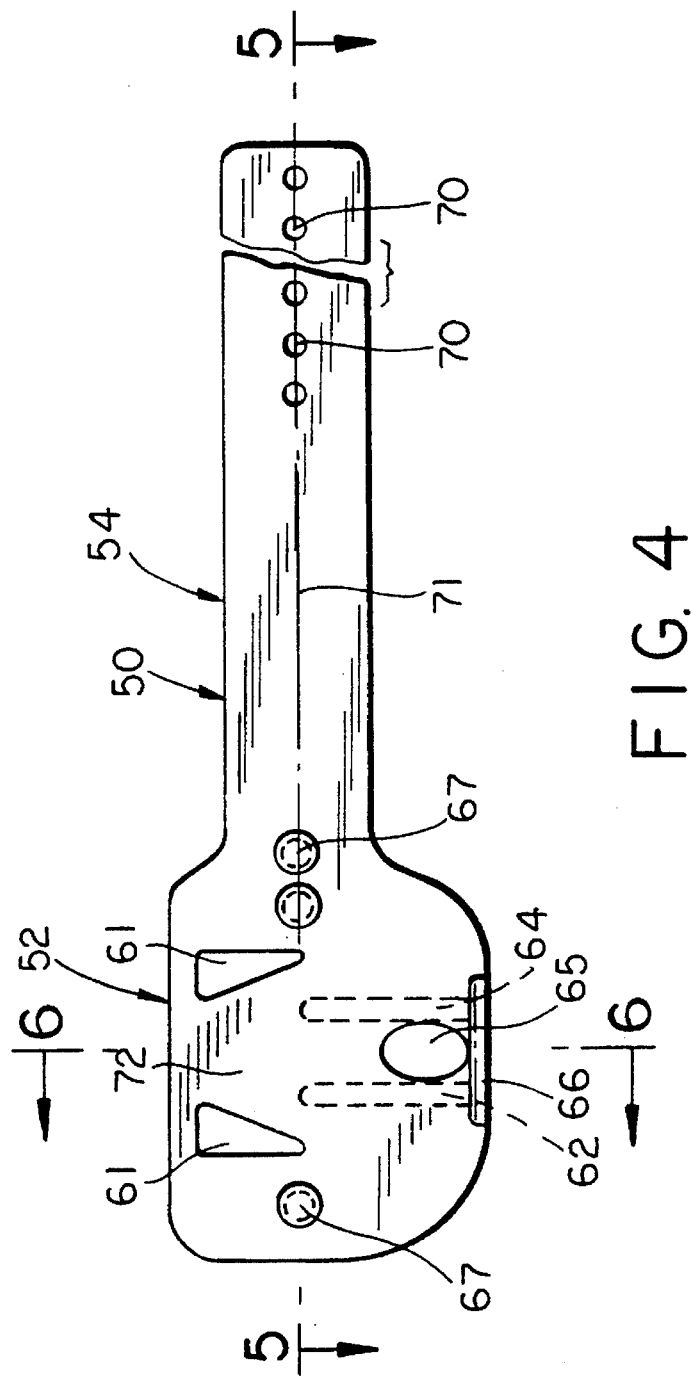

INFUSION ADMINSTERING CATHETER HOLDER

The present invention relates to medical appliances, and more particularly to a holder for securing infusion administrating catheters onto patient arms.

BACKGROUND OF THE INVENTION

Infusion administrating catheter devices are conventionally formed of two main portions—see FIG. 1—namely the head portion generally indicated at 10, and an elongated, flexible syringe needle sheath portion indicated at 12. The head portion comprises a double wing-like base 14, an inlet socket portion 16 for the plasma or other medical substance which is to be administered to the patient, and the venting branch 18 having an openable cover 20 which is connected to the branch 18 by a wire 22.

These constructional features of the administering catheter are standard and need not be further described.

It is a common practice in hospitals to attach the administering catheter 10 to the patient's arm or other limb portion, after insertion of a syringe (metal) needle into the vein (not shown), by a common medical adhesive tape. This primitive method of attaching the catheter has been used now for decades in spite of various disadvantages thereof, particularly the fact that every time that the catheter has to be removed, the adhesive tape must be ripped off, causing considerable pain to the patient.

It is thus the prime object of the invention to overcome the deficiencies of the conventional, non-sophisticated method.

It is a further object of the invention to provide an infusion catheter holder which is adapted to be easily attached and removed, as the case may be, without causing any inconvenience to the patient.

It is a still further object of the invention to provide a holder which is in form of a flexible band essentially adapted to be secured and removed by using releasable attaching means, such as VELCRO, zipper-like fasteners, mushroom fasteners, and the like.

SUMMARY OF THE INVENTION

Thus provided according to the invention is a holder for infusion administering catheter devices which comprise a head portion and a catheter portion. The holder is formed as a deformable band having a first portion configured to overlie the device in its administered position onto a patient's arm without obstructing access to its functional parts. A second portion is adapted to surround the arm portion of the patient and become tightened over the said first portion by releasable attaching means.

Said first portion may be provided with an opening through which the said head portion of the catheter is accessible, as well as with a pair of ribs extending at both sides of said opening.

These and further features and advantages of the invention will be readily understood in the light of the following description of preferred embodiments thereof, given by way of example only, with reference to the accompanying drawings.

DESCRIPTION OF THE DRAWINGS

In the drawings:

FIG. 3b is a sectional view taken along line III—III of FIG. 3a;

FIG. 4 is a plan view of a catheter holder according to another embodiment of the invention;

FIG. 5 is a cross-section of the catheter holder of FIG. 4, taken on plane V—V of FIG. 4, looking in the direction of the arrows;

DESCRIPTION OF PREFERRED EMBODIMENTS

Figure 1:
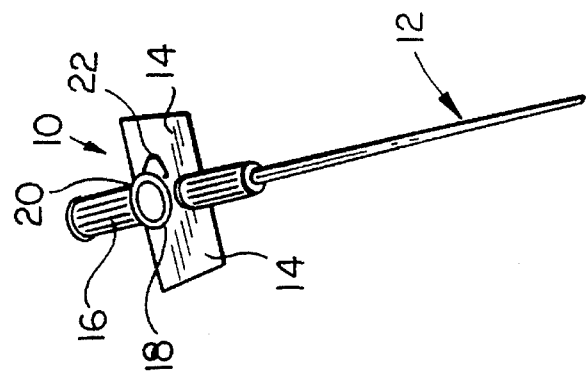
FIG. 1 represents a conventional infusion administrating catheter device.
Figures 2A, 2B:
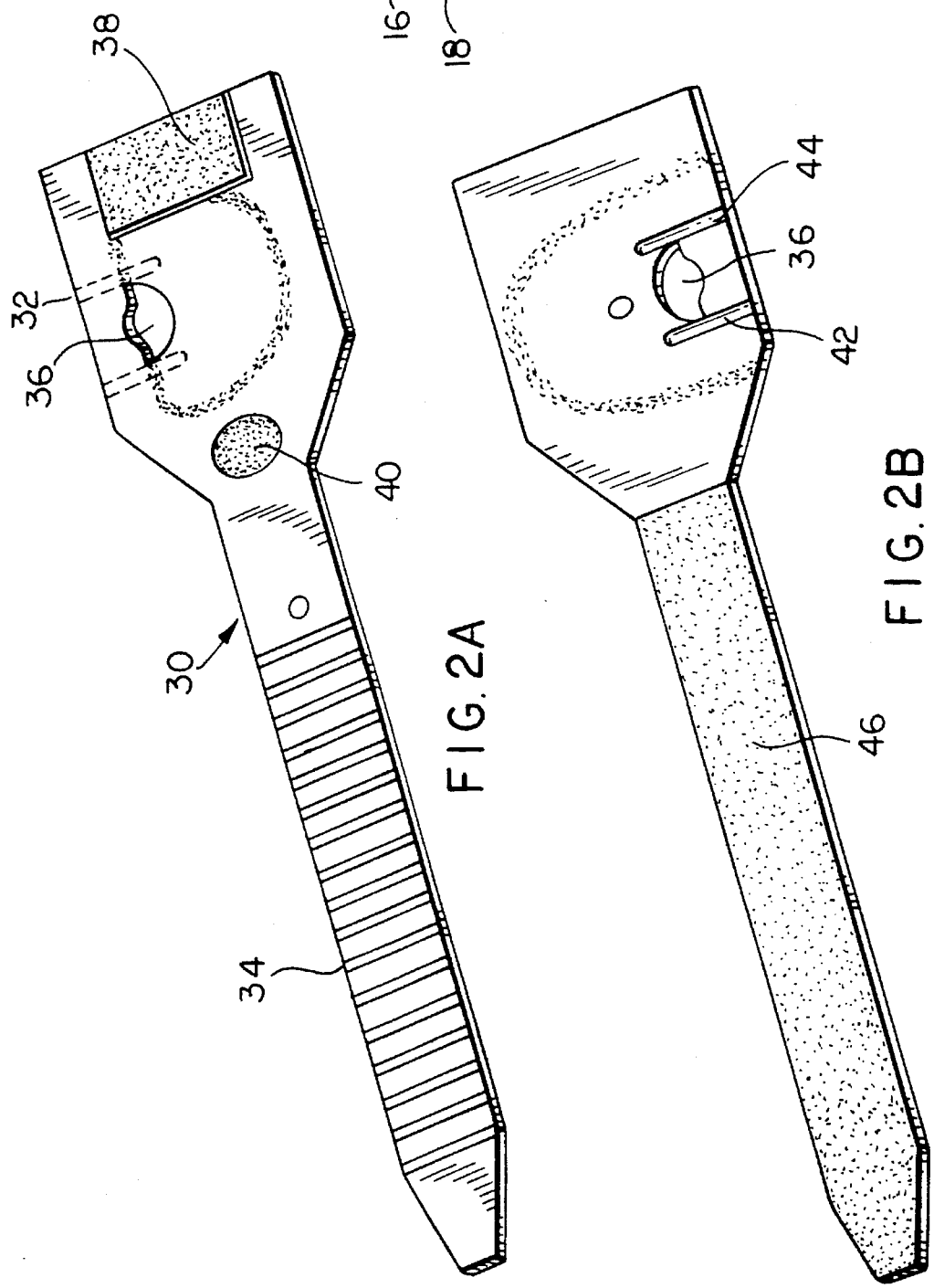
FIGS. 2a and 2b show a catheter holder according to an embodiment of the invention, from its outer and inner sides, respectively.

Referring to FIGS. 2a and 2b, there is shown a catheter holder, which in the form of a band generally indicated at 30, essentially comprising a catheter head covering and holding portion 32, and a strip portion 34, said two portions constituting a single piece similar to a wrist watch band.

The holder 30 is made of a bendable material such as leather, rubber or plastics.

Figure 3A:
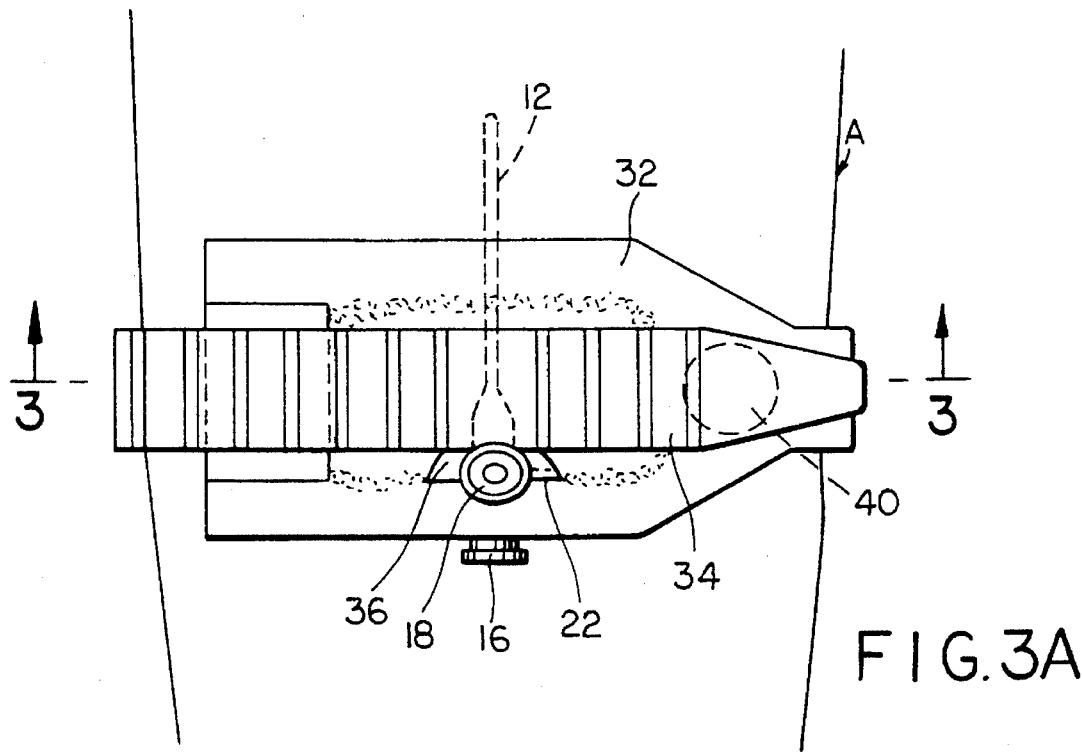
FIG. 3a is a top view of the holder according to the invention when worn by a patient.
Figure 3B:
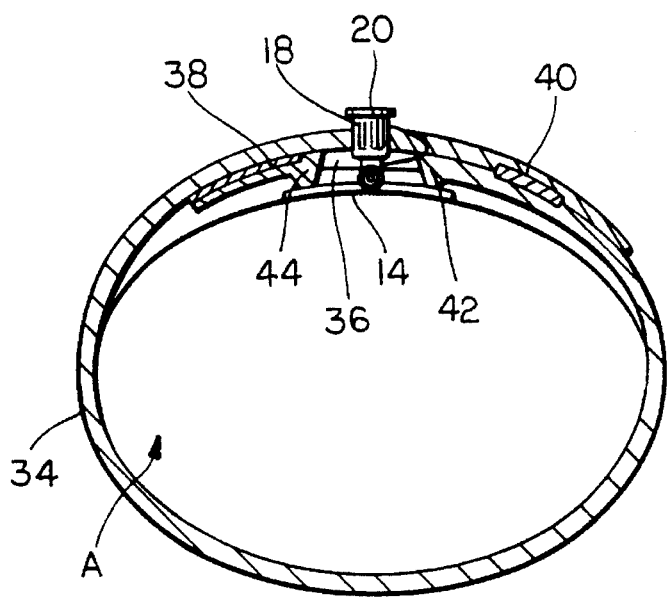

The portion 32 is provided with an oval opening 36, of such a size as to allow the projection therethrough of the portion 18 and related parts of the catheter device 10 (see FIGS. 3 and 3b).

At its upper side, shown in FIG. 2a, there are provided a first, preferably male, VELCRO lining piece 38, and a second male VELCRO lining piece 40.

The bottom side of strip portion 34 (FIG. 2b) is provided on all its length with female VELCRO lining 46, being so selected for its smoothness and consequent less irritating effect to the human skin. Optionally, a pair of ribs 42 and 44 are also provided at the bottom side of the band portion 32 for a purpose to be explained hereinafter.

In its operative state illustrated in FIGS. 3a and 3b, the band is worn by the patient by being wrapped abound the arm portion thereof, indicated at A, in the following manner: once the catheter device has been properly administered to the patient, namely once its portion 12 has been inserted into the patient's vein, and the head portion lies over the patient's skin—the first portion 32 is simply placed over it so that the branch 18 protrudes through the opening 36. As will be seen in FIG. 3a, ribs 42 and 44 are effective to stabilize the wings 14 against the patient's arm A. Thereafter, the band portion 34 is simply wound around the arm portion A and attached by its female VELCRO lining 46 against at least the lining 38 provided at the extreme end of the first portion 32, and possibly also by the VELCRO portion 40 (depending on the size of the arm). Thus the administering infusion catheter is safely secured to its place without use of additional means, thus completely superseding the primitive adhesive tape fixing method.

According to another embodiment of the invention, illustrated in FIGS. 4 to 7, the holder is made of elastic material and is stretchable to a certain extent, as will be specified later. The releasable attaching means are discontinuous male-female means, which will be generically called "core fasteners". By "core fastener" is meant herein any type of fastener which comprises a male element engageable in a complementary female element. Conveniently, a core fastener, as used in this invention, comprises a mushroom-shaped male element comprising a stem and head and a complementary opening which constitutes the female element, said male element being adapted to be inserted through said opening so that the head will pass through it and project from the opposite side of the opening. The head has a larger diameter than the complementary opening and squeezes therethrough because it is made of elastically deformable material, but, because of its diameter, will not be easily withdrawn from the opening, as will be better understood hereinafter. Therefore the particular fasteners illustrated in this embodiment will be called "mushroom fasteners".

Figure 6:
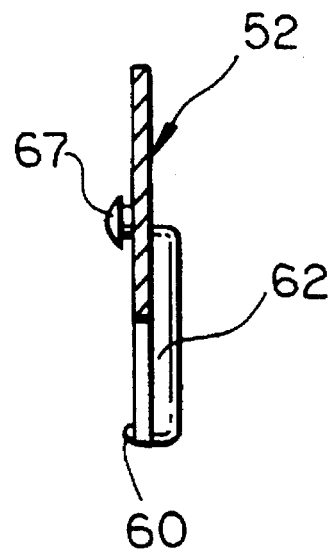
FIG. 6 is a cross-section of the catheter holder of FIG. 4, taken on plane VI—VI of FIG. 4, looking in the direction of the arrows.

More specifically, as seen in FIGS. 4 to 6, the catheter holder 50 is once again comprised of a catheter head covering and holding portion 52 and a band portion 54, corresponding to portions 32 and 34 respectively of the previous described embodiment. The holder is made of an elastic, stretchable material, such as a natural or synthetic rubber, particularly a silicone rubber, or more preferably a transparent resin known as BVS K-Resin [™] polymer, manufactured by Philips Petroleum Company, which resin has been found usable in the medical sector. BVS K-Resins conform to class VI-50 U.S.P. and may be used in contact with blood. They may be sterilized by using ethylene oxide or by submitting them to gamma rays. They are highly transparent and significantly extensible. However, other materials having similar characteristics can be used for carrying the invention into practice.

Figure 7:
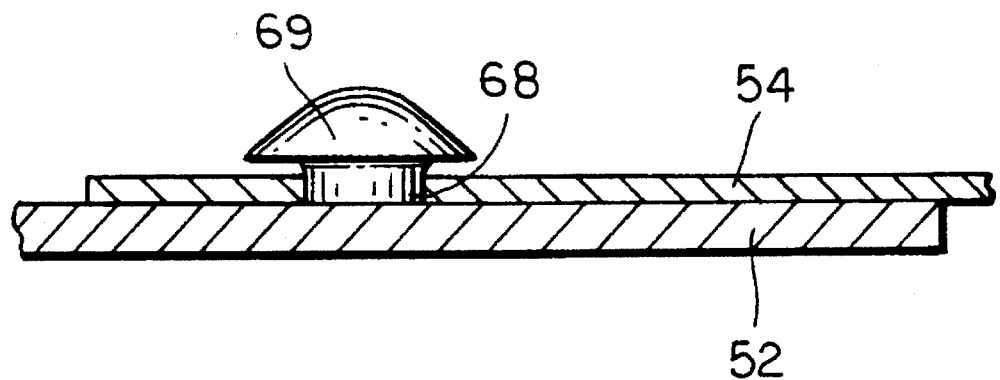
FIG. 7 is cross-section at an enlarged scale of a releasable fastener used in the embodiment of FIGS. 4 to 6, shown in its fastening condition.

As seen in FIGS. 4 to 6, the covering and holding portion 52 is provided, as the corresponding portion of the previously described embodiment, with ribs 62 and 64, effective to stabilize the wings 14 of the infusion administering catheter against the patient's body. It is also provided with oval opening 65 located between the two ribs, dimensioned so as to allow the projections therethrough of the portion 18 and related parts of the catheter device 10. An additional rib 66, perpendicular to ribs 62–64, is preferably provided on the opposite face of the portion 52, at the outer edge of opening 64. Additionally, portion 52 is preferably provided with substantially triangular openings 61, the purpose of which will be explained hereinafter. Finally, the portion 52 is provided with male members 67 of mushroom fasteners illustrated in this particular embodiment in the number of three. Each of said male elements, as best seen in FIG. 7 which shows, at an enlarged scale, a fastener in its engaged or fastening condition, comprises a stem 68 and a head 69, which, in this embodiment, are respectively cylindrical and disk-like with a circular edge.

The portion 54 of the device is provided with a number of apertures 70, which constitute the female elements of the mushroom fasteners and which, in this embodiment, are circular. The distance between the apertures 70 should preferably be such that the band portion 54 can be stretched by the same amount without applying such tension to it as to be uncomfortable to the patient. In this way, thanks to the stretchability of the band portion 54 of the device, the described fastening means, which is actually discontinuous and fastens in a stepwise manner, practically behaves like a continuous fastener.

The holder of this embodiment can be used like the holder of the first embodiment, simply by inserting the portion 12 of the catheter into the patient's vein, placing the head and cover portion 52 over the patient's skin, in such a way that the branch 18 of the catheter protrudes through the opening 65, and then winding the band portion 54 of the holder around the arm (or leg) of the patient and inserting one, and preferably two or all three of the male fastener elements 67 through one or more of the apertures 70. The disk-like heads 69 of the male elements will squeeze through the apertures, because their rim portions, of greater diameter than the stem portions 68, will fold elastically downwards; but once said heads have passed through the apertures 70, said rim portions will snap back elastically (as best shown in FIG. 7) and prevent the male elements 67 from being withdrawn from the apertures 70 unless considerable strength is exerted on them. Thus, thanks to the elasticity of the elements concerned, the two fastener elements are firmly connected together. Thanks to the number of apertures and the elasticity of the band portion 56, the holder can be applied around a patient's arm or leg of practically any size and firmly fixed in place by means of the mushroom fasteners. It is apparent, however, that differently structured fasteners, having comparable behavior, may be used by persons skilled in the art.

Once the holder is applied, it is subjected to a certain amount of tension, and this tension is applied along the axis 71 of the apertures 70. It will be seen that, due to the presence of the triangular openings 61, the tension accumulates, so to speak, in the narrow strip-like portion 72 of the cover portion 52, between the outer edge of openings 61 and the edge of the cover portion 52, thereby causing said portion more firmly to contact the patient's skin and better to secure the device in place.

It will be noted that in both embodiments the device can be used not only for placing about an arm or leg of a patient, but also for application on other parts of the body. Because the holder is provided with male and female fastener elements, additional straps provided with corresponding elements can be provided and therefore prolong, so to speak, the band portion 34 or 54. Not only that, but straps having male and female fastener elements can be connected to the device, in all its embodiments, in a perpendicular direction to that of the band portion 34 or 54, whereby to permit to apply the device to parts of the body that are not an arm or a leg, e.g., to the patient's chest. In this case, separate bands provided with fastener elements can act as suspenders and pass over the patient's shoulder, while other straps will serve to fasten the holder around the patient's chest.

It will be readily understood by those skilled in the art that various changes and modifications may be applied to the constructional features of the holder as above exemplified without departing from the scope of the invention as defined in and by the appended claims.

What is claimed is:

1. A holder for an infusion administering catheter device including a head portion and a catheter portion, said holder being formed as a deformable band, said holder comprising:

a first portion configured to overlie the device in its administered position onto a patient's arm without obstructing access to its functional parts;

a second portion formed as a band longer and narrower than said first portion, said second portion adapted to surround the arm of the patient to form a loop; and releasable attaching means for permitting said second portion to be tightened over said first portion at any desired position over the length of said second portion, whereby to form a loop of the desired circumference over the patient's arm.

2. The holder as claimed in claim 1, wherein said first portion of the holder has an opening through which said head portion is accessible.

3. The holder as claimed in claim 2, wherein said first portion of the holder comprises a pair of ribs extending alongside of said opening on the side of said first portion which contacts the patient's skin.

4. The holder as claimed in claim 3 wherein said first portion of the holder is provided with a first VELCRO fastener lining at its side facing away from the patient's arm portion, and said second portion is provided with at least a mating VELCRO fastening lining at its side facing the patient's arm and extending over a substantial length of said second portion.

5. The holder as claimed in claim 4 further comprising, a second VELCRO lining positioned a distance from said first VELCRO lining.

6. A holder as claimed in claim 1, made of an elastic, stretchable material.

7. A holder as claimed in claim 6, wherein the elastic, stretchable material is silicone rubber.

8. A holder as claimed in claim 6, wherein the elastic, stretchable material is a BVS K-Resin.

9. A holder as claimed in claim 6, wherein the releasable attaching means are constituted by complementary male and female elements.

10. A holder as claimed in claim 9, wherein the releasable attaching means are a plurality of core fasteners.

11. A holder as claimed in claim 10, wherein the core fasteners are mushroom fasteners.

12. A holder as claimed in claim 9 wherein the releasable attaching means comprise a plurality of female elements, constituted by apertures extending over a substantial length of said second portion of the holder, and male elements, constituted by matching projections provided in the first portion of the holder, whereby at least one of said male elements may be coupled with at least one of said female elements to form a loop having a desired circumference.

13. A holder as claimed in claim 12, wherein the projections constituting the releasable attaching means comprise a stem portion and a head portion wider than the said stem portion and adapted elastically to pass through the apertures which constitute the female elements and secure the said male elements to said female elements by their head portions being superimposed to the second portion of the device.

14. A device as claimed in claim 6, wherein the first portion thereof is provided with openings adjacent to the side thereof opposite to the side on which the openings through which the head portions of the catheter device is accessible, whereby to concentrate the longitudinal strain of the holder, when in use, to a zone close to said opposite side.

15. A holder as claimed in claim 11, formed as a single piece of elastic material, wherein the core fasteners are formed integrally with the holder itself.

16. A holder as claimed in claim 6, wherein the releasable attaching means are core fasteners comprising male elements, integral with the holder's first portion, and matching apertures within the holder's second portion, said second portion being stretchable by an amount at least equal to the distance between each two successive said apertures.

\* \* \* \* \*